United States Patent [19]
Whittaker et al.

[11] Patent Number: 5,932,410
[45] Date of Patent: Aug. 3, 1999

[54] ASSAY FOR THE DETECTION OF PROTEASES

[75] Inventors: Robert G Whittaker, West Pymble; Yan Yu, Randwick, both of Australia

[73] Assignee: Commonwealth Scientific and and Industrial Research Organization, Campbell, Australia

[21] Appl. No.: 08/793,483

[22] PCT Filed: Aug. 25, 1995

[86] PCT No.: PCT/AU95/00536

§ 371 Date: May 14, 1997

§ 102(e) Date: May 14, 1997

[87] PCT Pub. No.: WO96/06185

PCT Pub. Date: Feb. 29, 1996

[30] Foreign Application Priority Data

Aug. 25, 1994 [AU] Australia ................................ PM7693

[51] Int. Cl.⁶ .................................................. G01N 33/48
[52] U.S. Cl. .................................. 435/4; 435/23; 435/24; 530/323; 530/331; 530/330; 530/329
[58] Field of Search .................................. 435/4, 23, 24; 530/323, 331, 330, 329

[56] References Cited

U.S. PATENT DOCUMENTS 5,459,035  10/1995  Guerrero et al. ............................ 435/6

OTHER PUBLICATIONS

Whittaker, et al. Anal. Biochem. vol. 220: pp. 238–243, 1994.

Kuriyama, et al. Cancer Research vol. 41(10): pp. 3874–3876, Oct. 1981.

*Primary Examiner*—Elizabeth Kemmerer
*Attorney, Agent, or Firm*—Nixon & Vanderhye

[57] ABSTRACT

The present invention relates to a method of detecting the presence of an active protease in a sample. The method involves the following steps: (1) providing a solid support to which is attached a ligand reactive with a protease; (2) contacting the solid support with a sample suspected to contain the protease; (3) washing the solid support to remove material not bound to the ligand; (4) contacting the washed solid support with a solution containing a peptide ester substrate which is hydrolysed for the protease, and (5) detecting protons produced by hydrolysis of the peptide ester substrate. In addition, the present invention provide a prostate specific antigen substrate, the substrate being of the general formula; A-B-Tyrosine-ester in which A is acetyl or carbobenzoxy and B is 2 to 6 amino acids.

12 Claims, 4 Drawing Sheets

ASSAY FOR THE DETECTION OF PROTEASES

ASSAY FOR THE DETECTION OF PROTEASE

The present invention relates to a an assay for the detection of active proteases in samples, particularly samples of biological origin. In addition, the present invention relates to substrates having protease specificity.

During a study of mutant proteases the need arose for an assay method that could rapidly and accurately determine the activity and specificity of a large number of serine proteases produced in bacterial cultures.

Proteases of the serine (and thiol) families possess esterase activities which proceed at much faster rates than the cleavage of peptide bonds. Advantage was taken of this activity to develop an "esterase" assay which uses a pH indicator to visualise the hydrogen ion release caused by the action of proteases on peptide-ester substrates. A series of twenty compounds of the form, carbobenzoxy alanyl-X-methyl ester (Z-AX-OMe) were synthesised where "X" is one of the naturally occurring amino acids. These substrates were used in a 96 well microtitre plate assay to screen each mutant enzyme for activity and specificity. The reactions were followed visually or quantified using a standard ELISA plate reader. The esterase assay, using trypsin as a test enzyme and Z-Ala-Arg-OMe as substrate, was more sensitive as than traditional trypsin substrates (three times the rate obtained with benzoyl arginine ethyl aster and twenty times the rate of benzoyl arginine p-nitroanilide) (Whittaker et al., Analytical Biochemistry, 220, 238–243, 1994).

The success of this assay led us to question its possible broader use in the characterisation and quantification of proteases in research in general and in clinical enzymology in particular. For example the assay could be useful for the rapid characterisation of a protease/s being produced by tumours where comparison of the reaction profile against a selected species of ester substrates would identify and quantify the proteases and potentially give an indication of the tumour's metastatic potential.

A number of difficulties arise in using such an assay system for biological samples. These include the buffering ions in the sample and that some proteases are present at only very low levels. In order to at least partly ameliorate theme problems and to improve the specificity the present inventors have developed an assay method involving ligand capture of the protease. In one form this is achieved by combining an ELISA/Dot Immunobinding Assay (Allergy 50 (2); 119–125, 1995,Y. Yu) and the Esterase Assay.

Accordingly, in a first aspect the present invention consists in a method of detecting the presence of an active protease in a sample, the method comprising the following steps:

(1) Providing a solid support to which is attached a ligand reactive with a protease;
(2) Contacting the solid support with a sample suspected to contain the protease;
(3) Washing the solid support to remove material not bound to the ligand;
(4) contacting the washed solid support with a solution containing a peptide ester substrate which is hydrolysed by the protease; and
(5) Detecting protons produced by hydrolysis of the peptide ester substrate.

The ligand may be any of a number of binding molecules well known in the art. It is however, necessary that the ligand binds to the protease at a position which is not involved in the hydrolysis of the ester. It is presently preferred that the ligand is an antibody, preferably a monoclonal antibody or antibody fragment.

The peptide ester substrate may be any of a number of substrates hydrolyzed by the protease. Preferably, the substrate is hydrolysed rapidly by the protease.

By appropriate selection of the peptide ester substrate it in possible to add a further layer of specificity to the assay method. For example, use of ligand reactive with prostate specific antigen and a substrate which is specifically hydrolysed by prostate specific antigen will result in a highly specific assay method.

In a further preferred embodiment the production of a proton by the hydrolysis of the peptide ester is detected using a pH indicator. A pH indicator, such as phenol red, may be added after step 4, however, it is presently preferred that indicator is included in the solution added in step 4.

In another preferred embodiment the sample is serum or semen.

The method of the present invention could be used to detect the presence of a number of important mammalian proteases. These include:

| | |
|---|---|
| 1. | Tumour Markers |
| | Prostate specific antigen (PSA) |
| | Elastase - pancreatic antigen (PSA) |
| | Cathepsin B - breast cancer |
| | Urokinase type plasminogen activator |
| 2. | COagulation |
| | Kallikrein |
| | Factors II, VII, IX, XI, XII |
| | Protein C |
| | Tissue plasminogen activator |
| | Urokinase |
| | Streptokinase |
| | Plasmin |
| 3. | G I Tract Proteases |
| | Trypsin |
| | Chymotrypsin |
| 4. | Complement factors |

In a preferred embodiment of the present invention the method is to detect the presence of prostate specific antigen in the sample.

As will be apparent to persons skilled in the art the method of the present invention is similar in some aspects to a conventional ELISA. There are, however, a number of important advantages over conventional ELISA techniques. The first is that the method of the present invention detects only active proteases. Secondly the method of the present invention does not require a second antibody stage.

The present inventors have also developed better substrates for prostate specific antigen.

Accordingly in a second aspect, the present invention consists in a prostate specific antigen substrate, the substrate being of the general formula:

A-B-Tyrosine-ester in which A is acetyl or carbobenzoxy and B is 2 to 6 amino acids.

In a preferred embodiment of the present invention A is acetyl and B is ala-val.

In a further preferred embodiment the ester is a methyl aster.

In order that the present invention may be more clearly understood preferred forms thereof will now be described with reference to the following examples and Figures in which:

FIG. 1 shows the specificity profile of PSA and the proteases present in semen. The similarity of the profiles indicates that PSA is a major component of semen with another enzyme(s) with arginine and lysine specificity being present in the semen sample.

FIG. 2 shows semen and PSA profiles on substrates of the form Ac-Ala-x-TyrOMe. The similarity of the profiles indicates that PSA is most likely responsible for all the tyrosine activity in semen. PSA had a rate of 0.0263 $OD_{580}$ change/min/μg equivalent to 9.99 μmoles substrate/min/mg. Semen was 0.0416 $OD_{580}$ change/min/0.67 μl indicating that semen contained approx. 2.4 mg PSA/ml.

The present inventors sought to develop a "better" substrate for PSA by synthesising a range of substrates of the general formula:

Acetyl-Ala-X-Tyr-methyl ester

In all eleven compounds were synthesised and purified and tested where X was the residue listed below. The rates obtained with semen and PSA on these substrates are shown in FIG. 2.

TABLE 1

Esterase Rates of Selected Serine Proteases
Rates are $A_{580}$ change/min./mg protease. Rates are also shown as a percentage of the maximum activity to allow comparison. For elastase and α-lytic protease the results are normalised to alanine, the expected dominant preference.
Individual rates are approximately ± 10%.

| P1 Residue | Chymo-trypsin Rate | % | Trypsin Rate | % | Thrombin Rate | % | Elastase Rate | % | α-Lytic protease Rate | % | Subtilisin Rate | % | Proteinase K Rate | % |
|---|---|---|---|---|---|---|---|---|---|---|---|---|---|---|
| Ala | trace | | 0 | 0 | 0 | 0 | 15.7 | 100 | 6.2 | 100 | 1536 | 73.8 | 775 | 100 |
| Cys | 0.4 | 0.7 | 0 | 0 | 0 | 0 | 86.1 | 548.4 | 8.5 | 137.1 | 1251 | 58.2 | 392 | 50.6 |
| Asp | 0 | 0 | 0 | 0 | 0 | 0 | 0 | 0 | 0 | 0 | trace | | 18 | 2.3 |
| Glu | 0 | 0 | 0 | 0 | 0 | 0 | 0 | 0 | 0 | 0 | 83 | 3.9 | 97 | 12.5 |
| Phe | 37.8 | 68.5 | 2.9 | 0.8 | 0 | 0 | 0 | 0 | 0 | 0 | 998 | 46.0 | 342 | 44.1 |
| Gly | 0 | 0 | 0 | 0 | 0 | 0 | 0 | 0 | 0 | 0 | 22 | 1.0 | 58 | 7.5 |
| His | 1.5 | 2.7 | 3.0 | 0.8 | trace | | 0 | 0 | 0 | 0 | 249 | 11.6 | 203 | 26.2 |
| Ile | 0 | 0 | 0 | 0 | 0 | 0 | 1.7 | 11.0 | 0 | 0 | 16 | 0.7 | 5 | 0.6 |
| Lys | 1.5 | 2.7 | 155.8 | 44.0 | 4.3 | 49.0 | 0 | 0 | 0 | 0 | 153 | 7.1 | 61 | 7.9 |
| Leu | 2.4 | 4.3 | 0 | 0 | 0 | 0 | 3.4 | 21.7 | 0 | 0 | 1329 | 61.8 | 240 | 31.0 |
| Met | 6.6 | 12.0 | 0 | 0 | 0 | 0 | trace | | 2.0 | 32.3 | 2149 | 100 | 525 | 67.7 |
| Asn | 0.3 | 0.5 | 0 | 0 | 0 | 0 | 0 | 0 | 0 | 0 | 244 | 11.4 | 137 | 17.7 |
| Pro | 0 | 0 | 0 | 0 | 0 | 0 | 0 | 0 | 0 | 0 | trace | | trace | |
| Gln | 0.5 | 0.9 | 0 | 0 | 0 | 0 | 0 | 0 | 0 | 0 | 1308 | 60.9 | 553 | 71.4 |
| Arg | 1.1 | 2.0 | 355.4 | 100 | 8.7 | 100 | 0 | 0 | 0 | 0 | 97 | 4.5 | 24 | 3.1 |
| Ser | trace | | 0 | 0 | 0 | 0 | 0.4 | 3.6 | 0.7 | 11.3 | 366 | 17.0 | 348 | 44.9 |
| Thr | trace | | 0 | 0 | 0 | 0 | 3.1 | 19.7 | 4.2 | 67.7 | 123 | 5.7 | 90 | 11.6 |
| Val | 0 | 0 | 0 | 0 | 0 | 0 | 2.1 | 13.4 | 1.3 | 21.0 | 35 | 1.6 | 97 | 12.5 |
| Trp | 27.2 | 49.3 | trace | | 0 | 0 | 0 | 0 | 0 | 0 | 216 | 10.1 | 353 | 45.5 |
| Tyr | 55.2 | 100 | 10.8 | 3.0 | 0 | 0 | 0 | 0 | 0 | 0 | 345 | 16.1 | 80 | 10.3 |

| SUBSTRATE | X |
|---|---|
| 201 | Ala (A) |
| 204 | Glu (E) |
| 205 | Phe (F) |
| 208 | Ile (I) |
| 209 | Lys (K) |
| 213 | Pro (P) |
| 214 | Gln (Q) |
| 216 | Ser (S) |
| 218 | Val (V) |
| 219 | Trp (W) |
| 220 | Tyr (Y) |

The present inventors produced a panel of substrates carbobenzoxy alanyl-X-methyl eater (Z-AX-OMe) where X is one of the naturally occurring amino acids. The reactivity of these substrates with a number of serine proteases is set out in Table 1 and FIG. 1.

Figure 1:
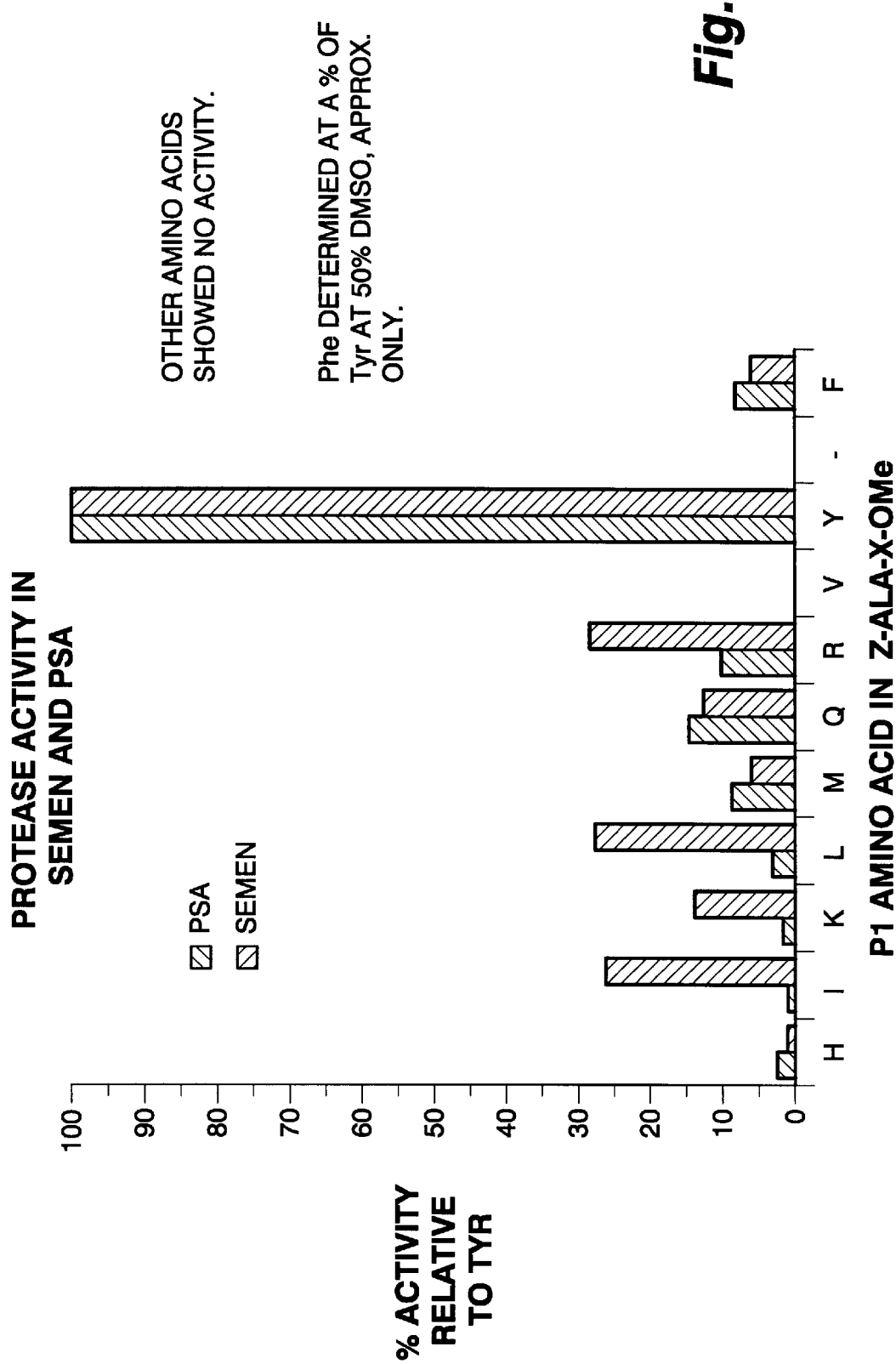

As expected from the literature these studies showed that of these substrates the preferred substrate for prostate specific antigen (PSA) was Z-AY-OMe (FIG. 1).

Figure 2:
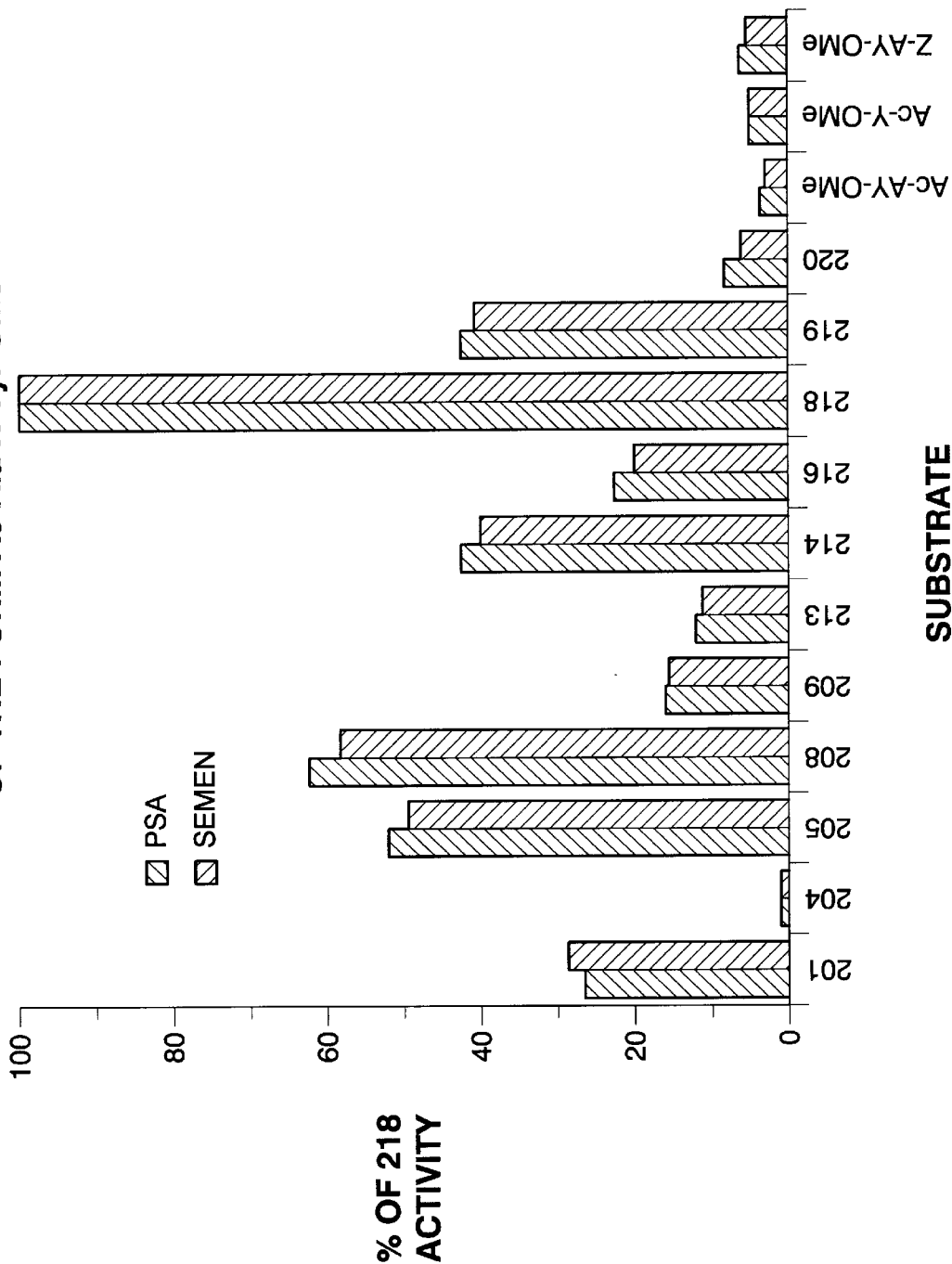

From FIG. 2, ten of the eleven substrates have improved activity over the original screening substrate Z-AlaTyr-OMe) and two other simple substrates (Ac-Tyr-OMe and Ac-Ala-Tyr-OMe).

The substrate Ac-AlaValTyr-OMe (218) proved to be the best for PSA. (Another substrate Ac-AlaLeuTyr-OMe was made subsequently and it had 70% of the rate of substrate (218).

The rate with Ac-AlaValTyr-OMe, from the graph, was 15.5 faster than Z-AlaTyr OMe (the screening substrate).

Figure 3:
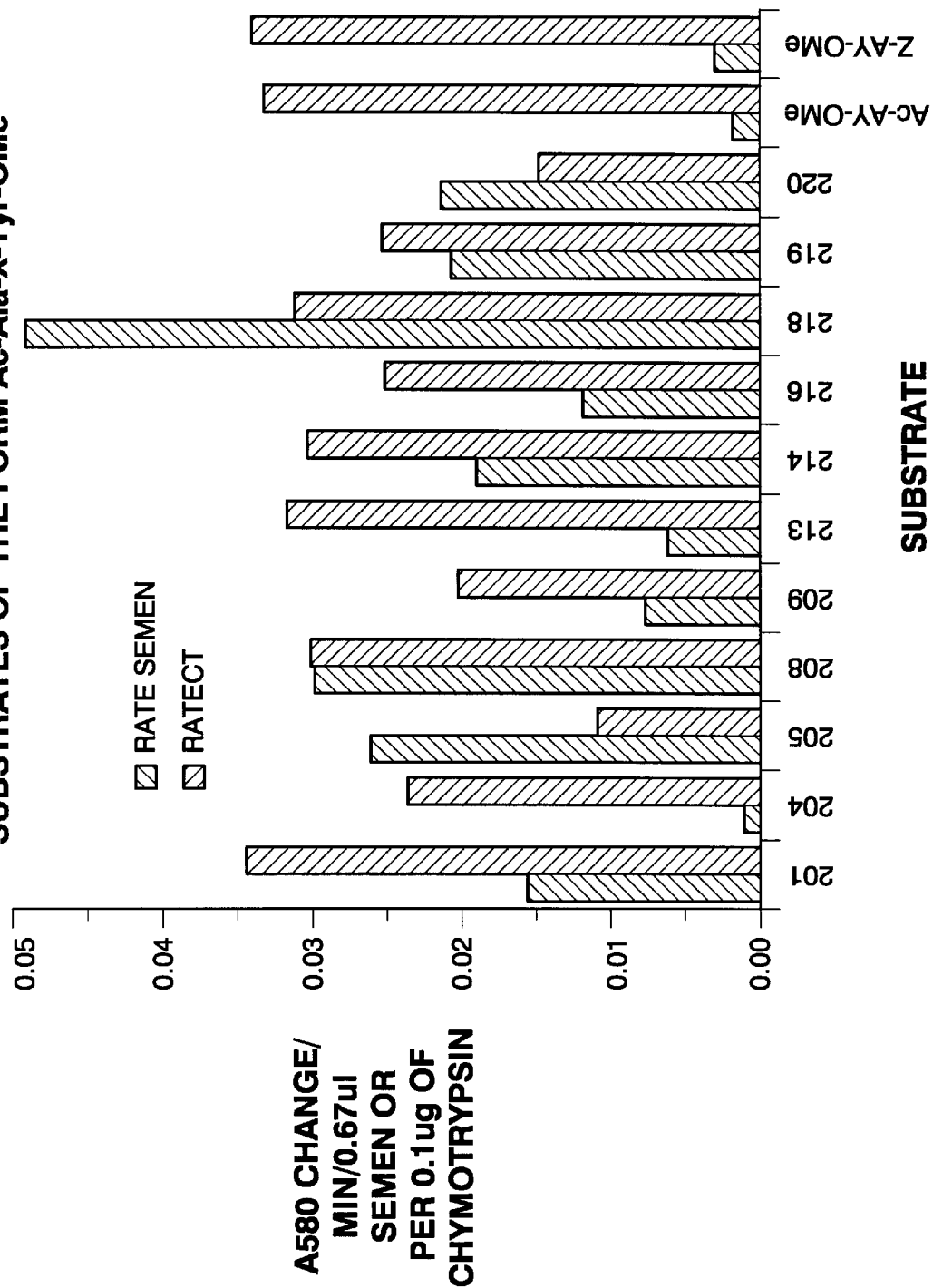
FIG. 3 shows activity of semen and chymotrypsin on substrates of the series Ac-Ala-X-Tyr-OMe. The different profiles support the contention that all of the Tyr activity in semen is due to PSA.

As shown in FIG. 2 the profile of PSA on the substrates was very similar to that obtained with semen indicating that the Tyr activity in san in predominantly due to PSA. The profile with the sane substrate set is widely diffrent from that obtained with chymotrypsin (FIG. 3) where there is no improvement in activity and widely varying rates on the various substrates. Clearly the more reactive substrates of the substrates are better reagents for an assay for PSA than was the screening substrate Z-Ala-Tyr-OMe.

There are obviously further improvements that could be made to the substrates, i.e., the next logical step would be to vary P3 and then P4. We have made one longer substrate, Ac-Val AlaValTyr-OMe, which gave a rate of 64.6% that of Ac-AlaValTyr-OMe. Obviously substituting Ac-Val for Ac in the P3 position has a deleterious effect on the rate of hydrolysis. This indicates that P3 and P4 are important and that other substitutions at P3 could possibly give a positive effective rate increase.

Figure 4:
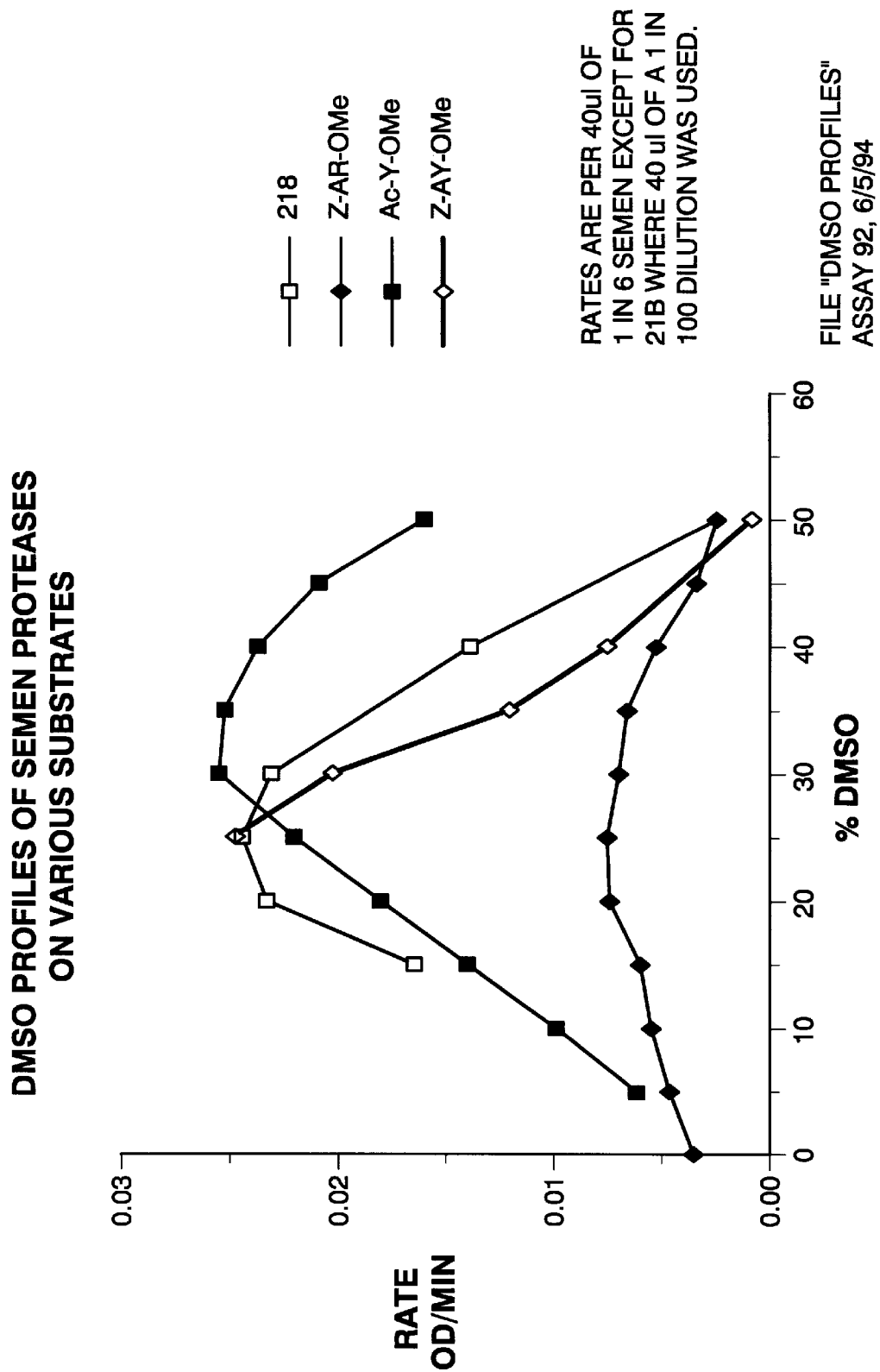
FIG. 4 shows profiles of semen proteases on various substrates with varying DMSO concentrations.

In these studies, the present inventors also made the surprising finding that activities of the serum proteases were optimal using substrates in 25–30% DMSO as opposed to an expected optimum of 0% solvent (FIG. 4).

Combination of Antibody Capture of PSA with Subsequent Detection of Active Protease via its Esterase Activity Method:
Step a) Nitrocellulose dots were treated with a solution of monoclonal anti-PSA antibody (MP077, PJ301, 4C1 SCRIPPS) at 1 µL/dot and dried O/N. (These can be stored at =20° C. for many months).

Step b) The dots were blocked against non-specific protein capture by a solution of 0.5% casein in Tris buffered saline (TBS, pH7.4) for 2 hours.

Step c) Diluted semen was applied to the dots and the PSA captured by the. monoclonal antibody. Non-binding components were removed by washing (TBS×2, 50 mM Bicine, pH 8.5×2).

Step d) The dots were placed in microtitre plate wells and overlayed with 40 µL Bicine buffer and 150 µL of 5 mM substrate 218 in 25% DMSO containing phenol red (concentrations as in normal assay).

Step e) The activity was detected visually by a colour change from purple red to yellow. This could be quantified by transferring the liquids to an new plate and reading in a Microtitre plate Reader using a filter at 570 nM.

A further improvement of the method would be to allow the capture phase and the esterase activity to be measured in the same vessel an in a conventional ELISA with the captured protease being detected by substrate overlay in the same well.

Experimental Design:

| | Blank well Dot 1 | Blank nitrocellulose membrane Dot 2 | No PSA capture Ab. Control Dot 3 | No semen Control Dot 4 | PSA capture + Semen Test Dot 5 |
|---|---|---|---|---|---|
| Step a) Capture (αPSA) | X | X | X | ✓ | ✓ |
| Step b) Blocking | X | ✓ | ✓ | ✓ | ✓ |
| Step c) Semen | X | X | ✓ | X | ✓ |
| Step d) Substrate | ✓ | ✓ | ✓ | ✓ | ✓ |
| Results | −ve Purple | −ve Purple | −ve Purple | −ve Purple | +ve Yellow approx 2 days |

Conclusion

PSA was "captured" from semen using the nitrocellulose dot with an attached monoclonal antibody directed against PSA. Immobilised PSA is in an active form as measured by the ester assay result (Dot 5).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method of detecting the presence of an active protease in a sample, the method comprising the following steps:

(1) providing a solid support to which is attached a ligand reactive with a protease;

(2) contacting the solid support with a sample suspected to contain the protease;

(3) washing the solid support to remove material not bound to the ligand;

(4) contacting the washed solid supported with a solution containing a peptide ester substrate which is hydrolyzed by the protease in which the peptide ester substrate is of the formula:

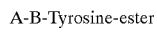

A-B-Tyrosine-ester in which A is acetyl or carbobenzoxy and B is 2 amino acids; and (5) detecting protons produced by hydrolysis of the peptide ester substrate.

2. A method as claimed in claim 1 in which the ligand is an antibody or antibody fragment.

3. A method as claimed in claim 2 in which the antibody is a monoclonal antibody.

4. A method as claimed in claim 1 in which the production of a proton by the hydrolysis of the peptide ester is detected using a pH indicator.

5. A method as claimed in claim 4 in which the solution added in step (4) further includes a pH indicator.

6. A method as claimed in claim 1 in which the sample is serum or semen.

7. A method as claimed in claim 6 in which the sample is semen.

8. A method as claimed in claim 1 in which A is acetyl and B is ala-val.

9. A method as claimed in claim 1 in which the ester is a methyl ester.

10. A prostate specific antigen substrate, the substrate being of the formula:

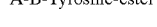

A-B-Tyrosine-ester in which A is acetyl or carbobenzoxy and B is 2 amino acids.

11. A prostate specific antigen substrate as claimed in claim 10 in which A is acetyl and B is ala-val.

12. A prostate specific antigen substrate as claimed in claim 10 in which the ester is a methyl ester.

* * * * *